United States Patent [19]
McDonald

[11] Patent Number: 5,351,991
[45] Date of Patent: Oct. 4, 1994

[54] FOLDED SHEET MEANS

[76] Inventor: George W. McDonald, Mon Cachet, Rue de la Cache, Castel, Guernsey, Channel Islands, Great Britain

[21] Appl. No.: 916,090
[22] PCT Filed: Dec. 4, 1991
[86] PCT No.: PCT/GB91/02154
  § 371 Date: Sep. 22, 1992
  § 102(e) Date: Sep. 22, 1992
[87] PCT Pub. No.: WO92/10828
  PCT Pub. Date: Jun. 25, 1992

[30] Foreign Application Priority Data
  Dec. 5, 1990 [GB] United Kingdom ............... 9026390

[51] Int. Cl.$^5$ ............................................. B42D 15/00
[52] U.S. Cl. ............................................. 281/2; 281/5
[58] Field of Search ................................. 281/2, 5

[56] References Cited

U.S. PATENT DOCUMENTS

2,354,066  7/1944  Sass ........................ 283/56
4,483,580  6/1989  Tuhkanen ................. 283/56

FOREIGN PATENT DOCUMENTS

0087987  9/1983  European Pat. Off. .
0157484  10/1985  European Pat. Off. .
0256672  2/1988  European Pat. Off. .
8704284  7/1987  .
8911140  11/1989  PCT Int'l Appl. .

Primary Examiner—Paul A. Bell
Attorney, Agent, or Firm—McAulay Fisher Nissen Goldberg & Kiel

[57] ABSTRACT

Sheet means (10) comprises a sheet of material (12) having mutually transverse sets of concertina folds (14, 16), sealing means (18, 20) to seal the same in a folded condition and defined opening means (18, 20), e.g. a marked and/or weakened break line (54) at which the sealing means can be opened, attachment means (36) for attaching the sheet means (10) to an article (28), diagonally opposite segments (22) of said sheet (12) being adapted one for attachment to the article and the other to be pulled free to open the sheet fully with a single movement once the sealing means have been opened. The penultimate section (80) and ultimate section (86) may project respectively beyond opposite sides (82, 88) of the underlying sections to allow adhesive strips (18, 20) to affix directly to the article (28) or only the ultimate thickness (segment) (26) may be extended (at 90) and so project. Sheet (12) may have a projecting tab (38) with adhesive portions (40, 46) that folds over to cover the main part of the sheet and attach it to an article or may have a separate cover piece, e.g. in the form of a loop (58) surrounding the folded sheet.

20 Claims, 2 Drawing Sheets

FOLDED SHEET MEANS

FIELD OF THE INVENTION

This invention relates to folded sheet means. It is known to affix information to articles by means of labels. There is an ongoing desire to increase the amount of information that can be provided and at the same time reduce the space available for this and labels have been designed in the form of a long, concertina-folded strip under a cover which seals the strip to the article until opened. However, this is not user-friendly because of the awkwardness of the handling of it and because of the awkward shape which confines the presentation of information.

THE INVENTION

The present inventor has appreciated that these difficulties can be solved by taking a sheet which has substantial breadth as well as length and folding it with a first set of concertina folds and, so as to be transverse to these when the sheet is folded with these folds, a second set of concertina folds. The use of sheet means comprising such a sheet and also sealing means to seal the same in a folded condition and defined opening means at which the sealing means can be opened may have wider application than simply attachment to an article. For example, it may constitute an article in its own right, for example a postcard, which combines the advantages of a wide sheet of information with a means for holding that information in sealed condition until required. The sheet means in this configuration has the advantage that the sheet can be fully opened with a single movement once the sealing means has been opened. When the sheet means are designed for attachment to an article they will comprise, for this purpose, attachment means, preferably in the form of adhesive means and a particularly user-friendly configuration is obtained if the said sheet has diagonally opposite segments defined by the concertina folds, one segment being adapted for attachment to the article and the other being adapted to be pulled free to open the sheet fully with a single movement once the sealing means have been opened. To make the sheet means further user-friendly, the opening means may comprise at least one marked and/or weakened break line.

In one embodiment of the sheet means, which is particularly convenient because it requires only a single sheet of material to be cut out, the sheet has a tab projecting from its back with, in order going from the main concertina part of the sheet, a first adhesive back portion, a fold line, a cover portion which folds over to cover the main part when this is folded and a second adhesive portion on the opposite face to the first. When the sheet is folded with both sets of concertina folds and the tab is folded at the fold line, the two adhesive portions face in the same direction and the cover portion can then seal the main portion to the article.

In another embodiment of the sheet means, there is attached to the said sheet a separate cover piece, preferably in the form of a loop surrounding the folded sheet and attached thereto at a back corner segment thereof, the sealing means being provided with the opening means in the region of the free end of the folded sheet.

In another embodiment, which particularly simplifies manufacture, the second set of concertina folds in folding the sheet is arranged so that the penultimate folded section extends beyond one side of the underlying folded sections and has on the lower face of the projecting part adhesive fixing means, and so that the ultimate section has at least the ultimate thickness thereof extending beyond the other side of the underlying sections and has adhesive fixing means on the underside of its projecting portion. Both of these adhesive means are intended to be able to be unsealed and possibly resealable. The very first thickness of the first section may have adhesive fixing means on its underside (if the sheet means is not intended to come free when the two said adhesive fixing means are unsealed). The whole may be provided on a backing or substrate which itself is provided with adhesive to affix the whole to the article.

With a view to making the sheet means even more user-friendly, the corner of the sheet which will be the front free corner when the sheet is folded comprises a demarcation of the corner, and the sheet carries a "pull" instruction on the demarcated corner and an arrow off the demarcated corner to show the direction of pulling to open the sheet fully with a single movement. Preferably, the sheet means are adapted for the "pull" instruction and arrow to be visible before the sealing means is opened.

For the purposes of the present specification, including the claims, "sheet material" is hereby defined as sheet material which has folds in it, regardless of whether it is in a folded up condition or not unless the context otherwise requires, and further is a material that takes folds at which it can be easily unfolded (without the folds disappearing) and refolded. It may be paper, or a paper-like material such as plastics sheet on which books are commonly printed, or may be very thin card or any other suitable flexible material. It is conceivable that the sheet material may be stiff except at the folds. e.g. very thin card inter-connected by paper or cloth, but this is deprecated as not allowing full realisation of the advantages of the invention.

it is to be noted that, while the sheet when folded may be of any size, it is particularly convenient to handle when of a size approximately that of a credit card, e.g. about four to eight centimeters width by about six to twelve centimeters length, preferably about five to five and a half centimeters width by about eight to eight and a half centimeters length.

The sheet may be reinforced and/or thickened in the region of the corner at which it is to be pulled to open the sheet fully.

It is found in practice that the sheet can not only be opened rapidly with a single movement but can also be refolded with both sets of concertina folds, rapidly, by reversing the same movement.

DESCRIPTION REFERRING TO DRAWINGS

Reference will now be made by way of example to the accompanying drawings, in which.

DESCRIPTION OF THE PREFERRED EMBODIMENTS

Figure 1:
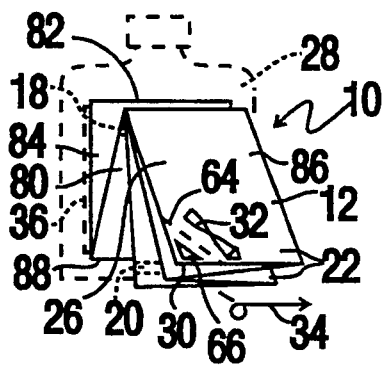
FIGS. 1 and 2 are perspective views of an embodiment showing the sheet nearly folded and nearly unfolded, respectively.
Figure 2:
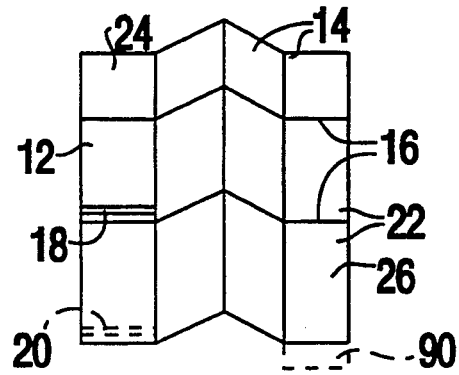

Referring to the drawings, and more particularly FIGS. 1 and 2, sheet means 10 embodying the invention comprise a sheet 12 of material as hereinbefore defined, having a first set of concertina folds 14 and, so as to be transverse to these when the sheet is folded with these folds 14, a second set of concertina folds 16, sealing means in the form of a strip of unsealable adhesive 18 on the front of sheet 12 and another strip 20 of the same on the back of sheet 12, each extending across only one segment 22 of sheet 12.

Figure 3:
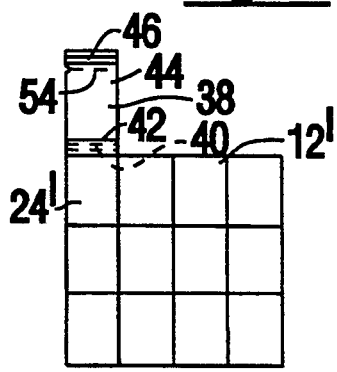
FIG. 3 is a plan (top) view (front view for reading purposes) of an embodiment with a covering tab, the sheet being shown unfolded.
Figure 4:
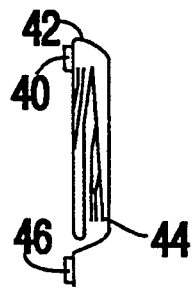
FIG. 4 is a diagrammatic side view of the same.
Figure 5:
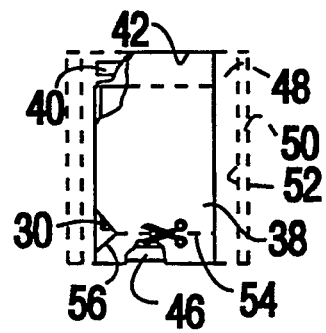
FIG. 5 is a partly cut-away similar view of the same in folded condition.

In use, sheet 12 carries information, e.g. printed text and diagrams, on both sides and is folded first at folds 14 concertina-wise and then at folds 16 concertina-wise to the form shown in FIG. 1. The sheet 12 has diagonally opposite segments 24, 26 defined by the concertina-folds 14, 16, one segment 24 being adapted for attachment to the article, e.g. bottle 28, and the other segment 26 being adapted to be pulled free to open the sheet fully with a single movement once the sealing means have been opened. In this embodiment, the bottle 28 is held in the left-hand and the corner 30 grasped between the finger and thumb (the thumb being on the underside of the segment 26) and the corner 30 is pulled in the direction of arrow 32, at the same time turning the right-hand over, so that sheet 12 is opened fully with a single movement, represented by arrow 34, to the position shown in FIG. 2. Adhesive means for attaching the sheet 12 to the article 28 are shown diagrammatically in FIG. 1 as a layer of adhesive 36 is on the back segment 24 the dot-dashed showing is intended to show that it is invisible in FIG. 1, though strips 18 and 20 may serve the same purpose, as described below. It may not be convenient for segment 26 to be free at the left and lower edges (as seen in FIG. 1) and a cover piece may be desirable for sheet 12. As shown in FIGS. 3, 4 and 5, the cover piece may be a tab 38 integral with sheet $12^I$ and projecting from its back segment $24^I$ with, in order going from the main concertina part of the set $12^I$, (in an upward direction as seen in FIG. 3), a first adhesive portion 40, a fold line 42, a cover portion 44 which folds over as seen in FIGS. 4 and 5 to cover the main part when this is folded, and a second adhesive portion 46 on the opposite face to the first adhesive portion 40.

In use, as illustrated in FIG. 3 the main (rectangular) part of sheet $12^I$ is folded in the same manner as sheet 12 as shown in FIGS. 1 and 2 and then the tab portion 38 is folded at line 42 to the position shown in FIGS. 4 and 5 so that portion 44 covers the main part of sheet $12^I$. The tab portion 38 may, as shown in dashed lines in FIG. 5, have wing portions 48 with adhesive strips 50 to affix the sides of tab 38 to the article (as well as the top and bottom edges of tab 38) and these may be unsealable or able to be torn at lines 52. Tab 38 forms part of the sealing means and its opening means comprise line 54 which is marked (e.g. with a diagram of a pair of scissors) or weakened by a line of perforations. Alternatively, adhesive sealing means 46 can be unsealable and possibly resealable. Preferably, tab 38 has a cut-out 56 to expose corner 30.

Figure 6:
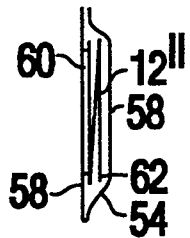
FIGS. 6 and 7 are views like FIGS. 4 and 5 of an embodiment with a cover piece in the form of a loop and FIG. 8 is a view similar to FIG. 7 of a variant with the folded sheet in the same position but the loop at right angles as that shown in FIG. 7.
Figure 7:
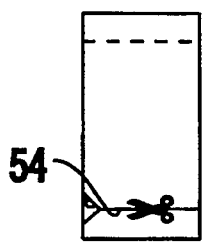
Figure 8:
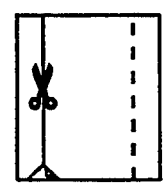

FIGS. 6, 7 and 8 illustrate embodiments comprising a separate cover piece 58 from sheet $12^{II}$, in the form of a loop surrounding the folded sheet $12^{II}$ and attached thereto at the back corner segment 24 thereof by means of an adhesive layer 60. The loop cover piece 58 constitutes the aforesaid sealing means and is provided with a marked and/or weakened break line 54 in the region of the free end 62 of the folded sheet $12^{II}$.

As may be seen more clearly in FIG. 1, the corner 30 of the sheet 12 which will be the front free corner when the sheet is folded comprises a demarcation 64 of the corner 30, and the sheet 12 carries a "pull" instruction 66 on the demarcated corner 30 and an arrow 32 off the demarcated corner to show the direction of pulling to open the sheet 12 fully with a single movement 34. By means of the cut-out 56, or the absence of a cover piece e.g. as in FIG. 1, or by use of a transparent cover piece 68 to be described in relation to FIG. 9, or otherwise, the sheet means 10 is adapted for the "pull" instruction 66 and arrow 32 to be visible before the sealing means is opened.

Figure 9:
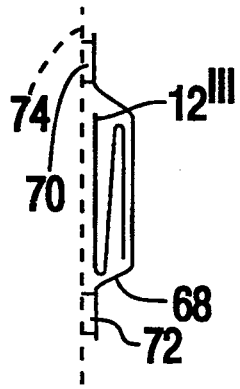
FIG. 9 is a view similar to FIG. 4 of an embodiment with a cover piece separate from the sheet.

FIG. 9 shows an embodiment in which there is simply provided a sheet $12^{II}$ and a separate cover piece 68, the latter having adhesive portions 70, 72 for affixing it to an article or to a substrate 74 which can itself be attached to an article by adhesive, or by other means as described below in connection with FIG. 12.

Figure 9A:
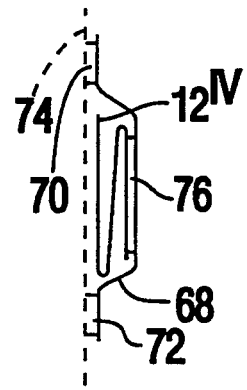
FIG. 9A is a modification of the FIG. 9 embodiment.

FIG. 9A shows another embodiment which is one variant of FIG. 9, in which sheet $12^{IV}$ has adhesive fixing means 76 for fixing it to cover piece 68, so that once the cover piece is opened, sheet $12^{IV}$ can be opened fully.

Figure 9B:
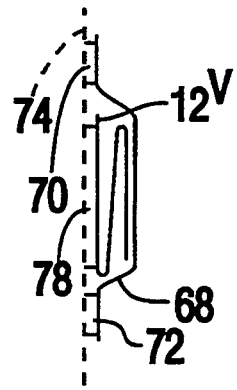
FIG. 9B is another modification of the FIG. 9 embodiment.

FIG. 9B shows another embodiment which is another variant of FIG. 9, in which sheet $12^V$ has adhesive fixing means 78 by which it can be fixed to the article or to substrate 74 any where desired both adhesive fixing means 76 and adhesive fixing means 78 can be used cojointly or individually.

Figure 10:
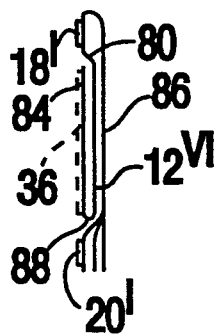
FIGS. 10 and 11 are views similar to FIG. 9 showing a variety of embodiments in which there is no cover piece, the sheet itself serving this purpose.
Figure 11:
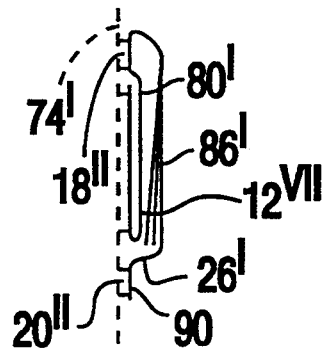

FIGS. 10 and 11 illustrate particularly advantageous variants of the FIG. 1 embodiment. In FIG. 1, the various segments 22 may all be of the same size, in which case strips $18^I$ and $20^I$ in FIG. 10 and $18^{II}$ in FIG. 11 fix different segments of the sheet itself. In FIGS. 10 and 11, sheet 12 has been designated as $12^{VI}$ and $12^{VII}$, respectfully. Alternatively, when the sheet 12 in FIG. 1 has been folded with the first set of concertina folds 14, the second set of concertina folds 16 can be arranged so that the penultimate folded section 80 projects beyond one side (upper edge 82) of the underlying folded sections (in FIG. 1 there is only one such section) 84 and has on the lower face of the projecting part adhesive fixing means $18^I$, and the ultimate folded section 86 is arranged so that the whole section 86 (as shown in FIG. 10) or at least the ultimate thickness thereof (segment $26^I$, as shown in FIG. 11) projects beyond the other side 88 of the underlying sections and has adhesive fixing means $12^{II}$ on the underside of its projecting portion. In the FIG. 10 embodiment, the bottom and left-hand edges of segment 26 (as seen in FIG. 1) will be free, while in the FIG. 11 embodiment there will be no free bottom edge to segment $26^{II}$ but this will require an extended projecting portion 90, shown also in dotted lines in FIG. 2.

Figure 12:
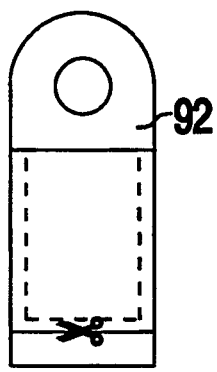
FIG. 12 is a view corresponding to FIG. 8 showing an alternative means for fixing the sheet means to an article.

While attachment means for attaching the sheet means to an article have been illustrated as adhesive (which may be for direct attachment as in the case of layer 36 or for indirect attachment as in the case of layer 78 and substrate 74), an alternative attachment means may be a loop 92, e.g. on substrate 74, as illustrated in FIG. 12. This can be passed over the cap of the bottle.

It will be apparent to those skilled in the art that various modifications and adaptations can be made. For example, it is possible to interchange or substitute one or more horizontal and vertical features, left-hand and right-hand features (e.g. opening), and upward or downward features (e.g. opening). Again, any one or more features of any embodiments may be applied to any other embodiments. For example, where opening means are shown as cut lines marked by diagrammatic scissors, these may be replaced by lines of weakening, e.g. slits or perforations.

In at least the FIG. 1 embodiment, the adhesive strips 18, 20 are able to be unsealed and thus serve not only as said sealing means but also as said defined opening means.

In all the embodiments, the sealing means comprises the opening means, and e.g. in FIG. 4 consists of tab 38 with adhesive means 40, 46 and in FIG. 6 loop 58, while in FIGS. 10 and 11 parts of the folded sheet itself form part of the sealing means.

I claim:

1. Sheet means comprising a sheet of material having a first set of concertina folds and, so as to be transverse to these when the sheet is folded with these folds, a second set of concertina folds;
   each of said concertina folds having at least three panels; and
   sealing means to seal the same in a folded condition, and defining opening means at which the seal means can be opened;
   said sheet having diagonally opposite segments defined by said concertina folds, one of said opposite segments being freely pullable to open the sheet fully with a single movement once said sealing means have been opened for opening said concertina folds.

2. Sheet means as claimed in claim 1, in which the opening means comprise at least one break line.

3. Sheet means as claimed in claim 1, comprising attachment means for attaching said one segment of said sheet means to an article.

4. Sheet means as claimed in claim 1, comprising adhesive means for attaching said sheet means to an article.

5. Sheet means as claimed in claim 1, including a tab projecting from the back of said sheet a first adhesive back portion for coupling said sheet to said article, a fold line, a cover portion which folds over to cover the main part when this is folded and a second adhesive portion on the opposite face to the first face.

6. Sheet means as claimed in claim 1, comprising a separate cover piece attached to said sheet.

7. Sheet means as claimed in claim 6, in which said separate cover piece is in the form of a loop surrounding said folded sheet and attached hereto at a back corner segment thereof, and opening means associated with said sealing means in the region of the free end of the folded sheet.

8. Sheet means as claimed in claim 1, wherein said opening means includes a "pull" means, a "pull" instruction and an arrow visible before said sealing means is opened.

9. Sheet means comprising:
   a sheet of material having a first set of concertina folds and, so as to be transverse to these when said sheet is folded with these folds, a second set of concertina folds;
   sealing means to seal the same in a folded condition and defined opening means at which said sealing means can be opened; and
   said second set of concertina folds being arranged so that the penultimate folded section projects beyond one side of the underlaying folded section/s and has on the lower face of the projecting part adhesive fixing means, and the ultimate folded section being arranged so that at least the ultimate thickness thereof projects beyond the other side of the underlaying sections and has adhesive fixing means on the underside of its projecting portion.

10. Sheet means as claimed in claim 9, in which said opening means comprise at least one marked break line.

11. Sheet means as claimed in claim 9, in which said sheet has diagonally opposite segments defined by said concertina folds, one segment being adapted for attachment to the article and the other segment being adapted to be pulled free to open said sheet fully with a single movement once said sealing means have been opened.

12. Sheet means as claimed in claim 9, in which said sheet has a tab projecting from the back, of a main concertina part of said sheet, a first adhesive back portion, a fold line, a cover portion which folds over to cover the main part when this is folded and a second adhesive portion on the opposite face to the first.

13. Sheet means as claimed in claim 9, comprising attachment means for attaching the sheet means to an article.

14. Sheet means as claimed in claim 9, comprising a separate cover piece attached to said sheet.

15. Sheet means as claimed in claim 14, wherein said attachment means includes adhesive means for attaching the sheet means to an article.

16. Sheet means as claimed in 14, including a separate cover piece in the form of a loop surrounding said folded sheet and attached thereto at a back corner segment thereof, said sealing means being provided with said opening means in the region of the free end of the folded sheet.

17. Sheet means comprising:
   a sheet of material having a first set of concertina folds and, so as to be transverse to these when the sheet is folded with these folds, a second set of concertina folds:
   sealing means to seal the same in a folded condition and defined opening means at which the sealing means can be opened: and
   said corner of said sheet which will be the front free corner when the sheet is folded comprising a demarcation of the corner, and said sheet carrying a "pull" instruction on the demarcated corner and an arrow off the demarcated corner to show the direction of pulling to open said sheet fully with a single movement.

18. Sheet means as claimed in claim 17, including means associated with said sheet carrying said "pull" instruction and said arrow for rendering thereof visible before said sealing means is opened.

19. Sheet means as claimed in claim 17, in which said sheet has diagonally opposite segments defined by the concertina folds, one segment being adapted for attachment to the article and the other being adapted to be pulled free to open the sheet fully with a single movement once the sealing means have been opened.

20. Sheet means as claimed in claim 17, including means associated with said sheet carrying said "pull" instruction and said arrow for rendering said "pull" instruction and said arrow visible before the sealing means is opened.

* * * * *